United States Patent [19]
Verhoff et al.

[11] Patent Number: 5,869,679
[45] Date of Patent: Feb. 9, 1999

[54] METHODS FOR PREPARING L-2-OXOTHIAZOLIDINE-4-CARBOXYLATE AND ITS CARBOXYLIC ACID

[75] Inventors: Francis H. Verhoff, Cincinnati, Ohio; L. Reade Baxley, Brandon, Fla.; Xiaofeng Lin, Wesley Chapel, Fla.; Gordon J. Rossiter, Lakeland, Fla.

[73] Assignee: Transcend Therapeutics, Inc., Cambridge, Mass.

[21] Appl. No.: 967,173

[22] Filed: Nov. 10, 1997

[51] Int. Cl.$^6$ .................................................. C07D 277/04
[52] U.S. Cl. ............................................................. 548/188
[58] Field of Search ............................................ 548/188

[56] References Cited

U.S. PATENT DOCUMENTS

| | | | |
|---|---|---|---|
| 3,628,971 | 12/1971 | Karchmar | 99/163 |
| 4,546,079 | 10/1985 | Metzger et al. | 435/71 |
| 4,647,571 | 3/1987 | Meister et al. | 514/369 |

OTHER PUBLICATIONS

Boettcher et al., Methods in Enzym., 113(5), 458–460, 1985.
Kaneko et al., Bull. Chem. Soc. Japan, 37(2), 242–44, 1964.

*Primary Examiner*—Johann Richter
*Assistant Examiner*—Laura R.C. Lutz
*Attorney, Agent, or Firm*—Pennie & Edmonds LLP

[57] ABSTRACT

Method for synthesizing L-2-oxothiazolidine-4-carboxylate and its acid, L-2-oxothiazolidine-4-carboxylic acid. The present invention involves the separation of phenol from a reaction mixture containing L-2-oxothiazolidine-4-carboxylate and phenol. In the present method a reaction mixture containing phenol, L-2-oxothiazolidine-4-carboxylate, and chloride salt, is contacted with a phenol adsorbing adsorption resin, the adsorption resin comprising a polymer having a polyethylene backbone. The adsorption resin is capable of adsorbing substantially all of the phenol while not adsorbing substantial amounts of the L-2-oxothiazolidine-4-carboxylate from the reaction mixture.

13 Claims, No Drawings

METHODS FOR PREPARING L-2-OXOTHIAZOLIDINE-4-CARBOXYLATE AND ITS CARBOXYLIC ACID

TABLE OF CONTENTS
1. BACKGROUND OF THE INVENTION
2. SUMMARY OF THE INVENTION
3. DETAILED DESCRIPTION OF THE INVENTION
4. EXAMPLES

BACKGROUND OF THE INVENTION

The present invention is directed to improved methods for preparing L-2-oxothiazolidine-4-carboxylate and its carboxylic acid, namely, L-2-oxothiazolidine-4-carboxylic acid. The present invention improves the separation of phenol from a mixture containing L-2-oxothiazolidine-4-carboxylate. The present method is simpler, less costly, safer to employ, and less toxic than the methods of the prior art.

U.S. Pat. No. 4,647,571 ("the '571 patent"), which issued to Meister et al., teaches that L-2-oxothiazolidine-4-carboxylate is an important compound in the intracellular delivery of L-cysteine in the body. Poisoning can occur by the excessive use of pain-killing drugs, such as those containing the active ingredients N-acetyl-para-aminophenol, paracetamol, and acetaminophen. Such drugs cause the level of glutathione in the liver to decrease. L-2-oxothiazolidine-4-carboxylate increases intracellular levels of L-cysteine (see, Meister, *Science* 220: 472 (1983)), which, in turn, increases the glutathione level in liver cells, which protects against the toxicity of such poisons.

The '571 patent also discloses that L-cysteine is relatively toxic extracellularly and therefore cannot be administered in significant quantities directly to the subject. See also Karlsen et al., *Brain Res.* 208: 167 (1981). The '571 patent teaches that by administering L-2-oxothiazolidine-4-carboxylate to the subject, L-cysteine is formed within the cells without the resultant toxicity which occurs when L-cysteine is administered extracellularly.

Either L-2-oxothiazolidine-4-carboxylate (i.e., the neutral salt form) or its carboxylic acid can be directly administered to the patient. For example, the salt is generally used for intravenous administration and the acid for administration by tablet. However, because the pH of blood is about 7, L-2-oxothiazolidine-4-carboxylate will be the active form in the body.

A number of methods exist for synthesizing L-2-oxothiazolidine-4-carboxylate and its carboxylic acid. Kaneko et al., *Bull. Chem. Soc. (Japan)* 37: 242–44 (1964), discloses that L-2-oxothiazolidine-4-carboxylate and its carboxylic acid can be synthesized by reacting L-cysteine with phosgene. Phosgene, however, is highly toxic and hazardous to use. Boettcher et al., *Methods in Enzymology*, 113(55): 458–60 (1985), discloses an improved method for synthesizing L-2-oxothiazolidine-4-carboxylate and its carboxylic acid, which uses phenyl chloroformate as a starting material instead of phosgene. The method disclosed in Boettcher et al. also results in higher product yields of L-2-oxothiazolidine-4-carboxylic acid than obtained when phosgene is used.

The reaction scheme of Boettcher et al. is generally as follows:

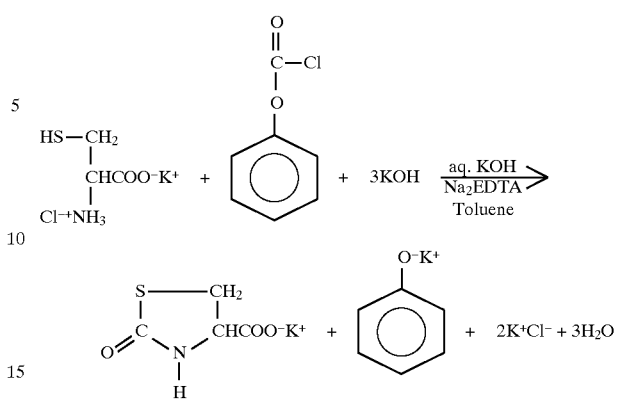

Generally, Boettcher et al. discloses that L-cysteine in an aqueous solution of potassium hydroxide and disodium ethylenediamine tetraacetate ($Na_2EDTA$) is reacted with additional potassium hydroxide and a mixture of phenyl chloroformate and toluene. This reaction yields the desired compound, sodium or potassium L-2-oxothiazolidine-4-carboxylate, as well as products consisting of the potassium and sodium salts of phenol and chloride. The solution is filtered to remove any particulate solids. The toluene layer is also removed. The aqueous layer or phase remaining, which contains L-2-oxothiazolidine-4-carboxylate and the salts of phenol and chloride, is acidified to a pH of about 6 to about 7 with hydrochloric acid so as to convert the potassium phenolate into phenol and additional potassium chloride.

The aqueous solution containing phenol, L-2-oxothiazolidine-4-carboxylate and potassium chloride is then contacted with diethyl ether in a staged manner to extract phenol from the aqueous solution into the immiscible diethyl ether phase. Boettcher et al. discloses that this extraction step is performed three times. The diethyl ether phase containing phenol is then separated from the aqueous phase containing L-2-oxothiazolidine-4-carboxylate. Thereafter the pH of the aqueous phase is further lowered to a pH of about 1 to about 2 by adding hydrochloric acid. This second pH adjustment converts the carboxylate to the carboxylic acid.

In Boettcher et al., L-2-oxothiazolidine-4-carboxylic acid is extracted from the aqueous solution with ethyl acetate which allows the potassium chloride to remain in the aqueous layer. The ethyl acetate layer is removed from the aqueous layer and the ethyl acetate is removed by evaporation. The resulting solid is dissolved in hot water and the L-2-oxothiazolidine-4-carboxylate is crystallized from this solution and dried. This product will be sieved for the correct particle size and packaged.

The addition of hydrochloric acid before and after extraction as disclosed in Boettcher et al. will add additional chloride ions to the aqueous layer containing L-2-oxothiazolidine-4-carboxylate to those already present in the solution as a normal byproduct of the chemical reaction between L-cysteine and phenyl chloroformate. Consequently, it is necessary to remove the original and additional potassium chloride to obtain the desired product.

The extraction and pH adjustment steps of the Boettcher et al. method are difficult to implement. The present invention greatly simplifies that method since the sequence of extraction steps utilizing diethyl ether or other extracting agent is replaced by contacting the reaction mixture in one step with an adsorption resin (however, multiple recycle steps can be used). The adsorption resin adsorbs at least about 90% and preferably about 95% to about 98% of the weight of phenol in the mixture and at most about 5%, preferably about 0% to about 3% of the weight of L-2-oxothiazolidine-4-carboxylate in the mixture. The improvement is also safer and less toxic than the Boettcher et al. method since it eliminates the need to use volatile and explosive extraction reagents such as diethyl ether. These benefits lead to a decrease in production cost when the process is carried out on a commercial scale.

The prior art discloses the removal of phenol by adsorption with an adsorption resin in applications other than the removal of phenol from a reaction mixture containing L-2-oxothiazolidine-4-carboxylate. For example, Mijangos et al., *J. Chem. Eng. Data* 40: 875–879 (1995) and Goto et al., *Environ. Sci. Technol.* 20: 463–467 (1986) discuss the adsorption of phenol using adsorption resins in the context of water pollutants. These applications, however, involve the removal of low concentrations of phenol. In the present invention, the concentration of phenol produced by the reaction is very high when compared to the concentration of the L-2-oxothiazolidine-4-carboxylate (about 0.64 kg phenol per 1.0 kg of compound). Based upon the teachings of these prior art references and upon the general concept that adsorption is used for removing materials of low concentration, one of ordinary skill in the art would not consider using adsorption to remove phenol from a solution of such high concentration as obtained in the synthesis of L-2 oxothiazolidine-4-carboxylate as described above, or in a similar manner.

SUMMARY OF THE INVENTION

The present invention is an improved method for preparing L-2-oxothiazolidine-4-carboxylate and its carboxylic acid, L-2-oxothiazolidine-4-carboxylic acid.

The present invention involves the separation of phenol from a mixture comprising L-2-oxothiazolidine-4-carboxylate and phenol, which comprises contacting the mixture with a phenol adsorbing adsorption resin, the adsorption resin comprising a polymer having a polyethylene backbone and the adsorption resin is capable of adsorbing at least about 90% of the weight of phenol in the mixture while adsorbing at most about 5% of the weight of L-2-oxothiazolidine-4-carboxylate in the mixture. In a further embodiment, the adsorption resin is separated from the solution remaining after the contact. In other embodiments, the solution remaining after separation is acidified to a pH of about 1 or 2 to form L-2-oxothiazolidine-4-carboxylic acid and the L-2-oxothiazolidine-4-carboxylic acid is crystallized. In still a further embodiment, the acidification is performed with an ion-exchange adsorption resin.

The present invention also relates to the synthesis of L-2-oxothiazolidine-4-carboxylate which comprises: (a) reacting L-cysteine with phenyl chloroformate and a base to form a mixture containing L-2-oxothiazolidine-4-carboxylate, phenolate salt, and chloride salt; (b) acidifying the mixture to a pH of about 6 to about 7 to convert the phenolate salt to phenol and removing any oil phase which forms; (c) contacting the acidified mixture from step (b) with a phenol adsorbing adsorption resin comprising a polymer having a polyethylene backbone, the adsorption resin capable of adsorbing at least about 90% of the weight of phenol in the acidified mixture while adsorbing at most about 5% of the weight of L-2-oxothiazolidine-4-carboxylate in the acidified mixture; and (d) separating the solution remaining after contact in step (c) from the adsorption resin. Other embodiments of the present invention further comprise acidifying the solution from step (d) to a pH of about 1 to about 2 to form L-2-oxothiazolidine-4-carboxylic acid and crystallizing the L-2-oxothiazolidine-4-carboxylic acid.

In another embodiment of this invention, the mixture containing phenol and L-2-oxothiazolidine-4-carboxylate is passed through a column packed with the adsorption resin.

In another embodiment the adsorption resin is a polystyrene polymer cross-linked with divinyl benzene, or a polyvinylpyridine polymer cross-linked with divinylbenzene, or a polyacrylic polymer.

In an additional embodiment of this invention, after the mixture is contacted with the adsorption resin and after the adsorption resin is separated from the solution remaining after contact, the adsorption resin is washed with water or an appropriate aqueous salt solution, including, but not limited to sodium chloride and potassium chloride, to remove the residual L-2-oxothiazolidine-4-carboxylate and/or phenol adhering to the adsorption resin.

In a further embodiment of this invention, after the adsorption resin is washed with water, it is stripped with either methanol or an aqueous hydroxide solution to remove the remaining adsorbed phenol so that the adsorption resin may be re-used.

In the present invention, the ease of separation of phenol from L-2-oxothiazolidine-4-carboxylate is surprising and unexpected since it would have been expected that L-2-oxothiazolidine-4-carboxylate, in a similar manner to phenol, would adsorb to the adsorption resin material. This separation is surprising and unexpected for several reasons. First, phenol is a hydrophobic compound, i.e., it is not very soluble in water. Hydrophobic compounds tend to be adsorbed on hydrophobic adsorption resins such as the adsorption resins used in methods of the present invention. Thus, it would be expected that better than 90% of the phenol would adsorb to such an adsorption resin. L-2-oxothiazolidine-4-carboxylate, however, contains both a carboxylate group which is hydrophilic (i.e., soluble in water) and a ringed portion which is hydrophobic. It is known that this ringed portion is hydrophobic because reactions carried out with esters of L-2-oxothiazolidine-4-carboxylate or L-cysteine in organic solvents indicate that such esters are not soluble in water. Because L-2-oxothiazolidine-4-carboxylate is partly hydrophobic it would have been expected that about 10% or more of the L-2-oxothiazolidine-4-carboxylate would be adsorbed to the adsorption resin. By the methods of the present invention at least about 90% and even as much as about 95% to about 98% of the weight of phenol in the mixture is adsorbed and at most about 5% and preferably about 0% to about 3% of the weight of L-2-oxothiazolidine-4-carboxylate in the mixture is adsorbed.

Second, common surfactants, i.e., compounds wherein one end is hydrophobic and one end is hydrophilic, such as long chain fatty acids, readily bind to the adsorption resins disclosed herein. Thus, it would have been expected that L-2-oxothiazolidine-4-carboxylate, which also possesses a hydrophobic and hydrophilic portion, would also bind to such adsorption resins.

Third, generally it is considered that cyclic compounds tend to be miscible with other cyclic compounds. Thus, it would have also been expected that because of the cyclic backbone which make up the molecules in polystyrene adsorption resins and polyvinylpyridine adsorption resins as described herein, L-2-oxothiazolidine-4-carboxylate and phenol, which are both cyclic, would also both adsorb to these two types of adsorption resins.

Surprisingly, L-2-oxothiazolidine-4-carboxylate remains in solution and the separation of phenol is almost quantitative. The simplicity of the present adsorption step permits a less expensive and more efficient method of synthesizing L-2-oxothiazolidine-4-carboxylate and, in turn, L-2-oxothiazolidine-4-carboxylic acid.

DETAILED DESCRIPTION OF THE INVENTION

The present invention improves the removal of phenol from L-2-oxothiazolidine-4-carboxylate. By way of example, the method of the present invention is a modification of the method disclosed in Boettcher et al., described above, which uses phenyl chloroformate and L-cysteine as starting materials. The present invention is also applicable to any other reaction process for the production of L-2-oxothiazolidine-4-carboxylate which forms phenol as a byproduct which must be separated out in order to form L-2-oxothiazolidine-4-carboxylate or its carboxylic acid.

As described above, after the reaction of L-cysteine with phenyl chloroformate, L-2-oxothiazolidine-4-carboxylate, potassium and sodium salts of phenol and chloride are produced. The hydroxide solution used in the initial reaction will determine the type of chloride and phenolate salts present in the reaction mixture. Thus the methods of the present invention are applicable for the separation of phenol when the initial reaction of phenyl chloroformate and L-cysteine is performed using hydroxides such as, sodium hydroxide, ammonium hydroxide, calcium hydroxide, and magnesium hydroxide as well potassium hydroxide as used in the experiments of Boettcher et al. described above. At this point the pH of the reaction mixture is about 10. To convert the phenolate salt to phenol and additional chloride salt, the pH of the reaction mixture can be adjusted from a pH of about 10 to a pH of about 3 to about 8 using hydrochloric acid or other acid such as sulfuric acid. Preferably the pH is adjusted to about 6 to about 7. Most preferably to about 7. At this point any oil phase which may be present is removed in a manner as would be known to one skilled in the art.

In the Boettcher et al. method, phenol is removed from the solution by multiple extractions with diethyl ether. In the present invention instead of using multiple extractions with diethyl ether or another solvent, the reaction mixture is contacted with an adsorption resin to adsorb phenol from the solution, leaving L-2-oxothiazolidine-4-carboxylate in solution. The present invention is, therefore, also suitable as a replacement for other methods which utilize other reagents to remove phenol. Such extraction reagents include, but are not limited to, chloroform, carbon tetrachloride, methylene chloride, other ethers, acetone, ethanol, benzene, and any other reagent which is relatively insoluble in water and wherein the solubility of phenol is greater in such reagent than in water. Such solvents all have some hazardous aspects. The chlorinated solvents have toxic effects and disposal problems. The ethers and esters are very volatile and are explosive hazards especially when used in large quantities for production. Therefore, there are significant safety hazards when using extraction for removal of phenol from the reaction mixture. The adsorption process of the present invention does not have these shortcomings.

In the methods of the present invention, the adsorption resin can be contacted in any way known in the art, such as, using a stirred vessel wherein the mixture containing phenol, L-2-oxothiazolidine-4-carboxylate, and the adsorption resin are placed. The adsorption resin is removed from the liquid by filtration. This process is discussed in Geankoplis, C. J., *Transport Processes and Unit Operations*, Prentice Hall, Englewood Cliffs, N.J. 07632, 3d Ed. (1993) pp. 700–701 and Weber, W. J. *Physicochemical Processes for Water Quality Control*, Wiley Interscience (division of John Wiley & Sons, Inc.), New York, N.Y. 10016 (1972) pp. 213–219, 242–243. Alternatively, it is particularly preferred that the contact be made by passing the reaction mixture containing L-2-oxothiazolidine-4-carboxylate and phenol through a column packed with a bed of phenol adsorbing adsorption resin. Suitable adsorption resins for the present method are those comprised of a vinyl polymer i.e., having a polyethylene backbone, including not limited to polystyrene, polyvinylpyridine, and polyacrylic. Particularly preferred polymers are polyvinylpyridine polymers cross-linked with divinyl benzene which are currently sold as Reillex resins by Reilly Industries, Indianapolis, Ind. such as Reillex HP;

polystyrene polymers cross-linked with divinyl benzene which are currently sold as DOW XUS 40285 and Rohm and Haas XAD-4 respectively by Dow Chemical Corp. Midland, Mich. and Rohm and Haas Corp., Philadelphia, Pa.; and polyacrylic polymers which are currently sold as XAD-7 by Rohm and Haas Corp. The most preferred adsorption resin is Reillex HP.

The diameter and height of the column or columns employed depends upon the rate at which feed solution is to be treated, the frequency of regenerating the adsorption resin, and the separation efficiency required. The column is first equilibrated with water, the water used in this steps and the steps described herein being most preferably deionized water. The feed solution containing phenol and L-2-oxothiazolidine-4-carboxylate is passed through the column at a rate of about 0.02 to about 0.09 bed volumes per minute. Preferably, the rate is about 0.025 bed volumes per minute. Most preferably the rate is about 0.03 bed volumes per minute. The amount of feed solution that is passed through the column depends upon the size of the column and the amount of phenol to be adsorbed. Typically, this is about 2 to about 6 bed volumes and preferably about 4 bed volumes. The time required to pass the feed solution through the column is dependent upon the flow rates and bed volumes and can be easily calculated by one skilled in the art.

After the solution is eluted from the column and collected, thereby separating it from the adsorption resin, wash water (optionally containing an inorganic salt) is added to the column at suitable rate, which can be about the same rate at which the feed solution is added. The amount of wash water added depends upon the percentage of recovery and the purity of the product required. The residual amount of L-2-oxothiazolidine-4-carboxylate eluting with the wash water will be added to the original eluent, or alternatively, the wash water containing L-2-oxothiazolidine-4-carboxylate can be recycled. Wash water which does not contain L-2-oxothiazolidine-4-carboxylate is discarded along with the phenol containing stripping liquid.

After the wash step, essentially all of the L-2-oxothiazolidine-4-carboxylate has been removed from the column. Thereafter, methanol or aqueous 4% sodium hydroxide is added at about the same rate as the feed solution was added (this rate can potentially be faster, such adjustments being known to one skilled in the art), in order to strip the remaining phenol from the adsorption resin. Preferably, aqueous sodium hydroxide is used as the stripping solution because there are no explosion or flammability considerations with this stripping solution. The amount of solvent used to strip phenol from the adsorption resin depends upon the efficiency of the solution in removing the phenol from the adsorption resin. It is desired, but not necessary, that practically all of the phenol be stripped from the column. After the resin is stripped it can be reused to separate phenol from additional reaction mixture.

Each of the above-described steps of the process is preferably performed at room temperature and atmospheric pressure (1 atm.); however, the temperature and pressure can also be varied such that the temperature is about 0° C. to about 50° C. and the pressure is about ½ atm to about 10 atm. The solvents used in the present process are also all at room temperature.

As described above, the Boettcher et al. process requires that the pH of the solution containing L-2-oxothiazolidine-4-carboxylate be adjusted in at least two instances. The first adjustment takes place after the reaction between L-cysteine and phenyl chloroformate wherein hydrochloric acid is added to acidify the mixture from a pH of about 10 to a pH of about 6 to about 7. By doing so, potassium phenolate and hydrochloric acid form phenol and potassium chloride, allowing for the extraction of phenol by diethyl ether. The second pH adjustment occurs after the extraction of phenol, but prior to crystallization. Here, hydrochloric acid is added again so that the pH is lowered from about 6 to about 7 to a value of about 1 to about 2 so that L-2-oxothiazolidine-4-carboxylate can be converted to its carboxylic acid (L-2-oxothiazolidine-4-carboxylic acid). The addition of hydrochloric acid or another acid, such as sulfuric acid, in both of these steps creates more anions in solution than what was already present as a byproduct of the reaction. These additional anions present in the solution must be separated from the final product. In Boettcher et al., ethyl acetate is used to extract the final product, L-2-oxothiazolidine-4-carboxylic acid, from the chloride anions or potassium chloride in solution.

In the present invention, the acidification steps can be performed in a similar manner or alternatively, they can be performed using an ion-exchange adsorption resin wherein the adsorption resin is modified with hydrogen ions. When the reaction mixture containing phenol and L-2-oxothiazolidine-4-carboxylate is contacted with the adsorption resin the hydrogen ions on the adsorption resin exchange with the potassium ions (or other cations if a different base was used in the initial reaction mixture) in solution. The hydrogen ions combine with the chloride ions already in solution, thereby acidifying the reaction mixture without adding more chloride ions (or other anions if a different acid is used) to the solution as in the methods of the prior art where hydrochloric acid is added. Similarly, after the phenol removing step, the solution containing L-2-oxothiazolidine-4-carboxylate substantially free of phenol can be contacted with additional adsorption resin modified with hydrogen ions to permit another exchange of hydrogen ions for potassium ions present in solution, thereby acidifying the solution. Such contact may be performed in the same manner as described above.

Adjustment of the pH using an ion-exchange adsorption resin prevents a greater accumulation of anions in solution, thus permitting a cleaner crystallization of the final product, namely, L-2-oxothiazolidine-4-carboxylic acid. If in the initial reaction between L-cysteine and phenyl chloroformate another hydroxide reagent is used other than potassium hydroxide, such as sodium hydroxide, ammonium hydroxide, calcium hydroxide, or magnesium hydroxide, the ion-exchange can be performed in an analogous manner.

After the phenol is separated from L-2-oxothiazolidine-4-carboxylate and the carboxylic acid is formed by acidification, the carboxylic acid is separated from the solution containing the carboxylic acid and the potassium (and/or other cation) chloride salts by crystallizing the carboxylic acid from this solution as would be performed by one skilled in the art. If the purity of the carboxylic acid is not sufficient with a single crystallization, it can be redissolved in water and recrystallized. If necessary, the carboxylic acid can later be readily converted back to a carboxylate salt i.e., L-2-oxothiazolidine-4-carboxylate, by methods known to one of ordinary skill in the art. Depending upon solubility constraints, this carboxylate salt can include a cation chosen from the group consisting of sodium, potassium, magnesium, calcium, iron, zinc, copper, selenium, manganese, and molybdenum.

Surprisingly and unexpectedly at most about 5% and preferably from about 0% to about 3%, of the weight of L-2-oxothiazolidine-4-carboxylate in the mixture binds to the adsorption resins. In addition to the polystyrene, polyvinylpyridine, and polyacrylic resins, it was thought that other resins might be useful to practice the invention. In particular, it was believed that a phenol formaldehyde resin would be useful because such resin is similar in structure to phenol and therefore should successfully adsorb phenol from the reaction mixture while leaving the L-2-oxothiazolidine-4-carboxylate in solution. An epoxy amine resin was also tested. Both the phenol formaldehyde and epoxy amine resin, which are resins not comprised of a polyethylene backbone, however, were not successful.

EXAMPLES

The following examples are provided only for the purpose of illustrating the invention and are not to be construed as limiting the invention in any manner.

To demonstrate the operation of the phenol adsorption from the reaction mixture containing L-2-oxothiazolidine-4-carboxylate, experiments were performed with a simulated reaction mixture. The following adsorption resins tested and described herein are: Dow XUS 40285, Rohm and Haas XAD-4, Rohm and Haas XAD-7, and Reillex HP.

Example 1

The feed solution was prepared in the following manner: Into a beaker was placed 0.190 kg of L-2-oxothiazolidine-4-carboxylate sodium. To this was added 0.252 kg of deionized water and these materials were mixed. The pH of this mixture was titrated to between 7 and 8 using 4N sodium hydroxide. To this mixture was added 1.138 kg of deionized water. Then 0.129 kg of sodium chloride were added followed by the addition of 0.132 kg of phenol. The mixture is stirred for ten minutes and left standing for 4 hours. Some of the phenol is separated into a top layer which is removed. The bottom layer is used as the feed solution for the tests.

A glass column of 15 mm internal diameter and 600 mm high was equipped with connectors and inlet and outlet tubing. A pressure gauge was provided on the inlet tubing. The column was half filled with deionized water and 100 ml. of Reillex HP adsorption resin was added to the column while the column was gently tapped with a rod. This adsorption resin was then washed with deionized water.

A variable rate pump was provided to supply the solutions to the tubing leading to the inlet of the column. The pump was started on deionized water at a rate of 6 ml/min. and was run until 4 bed volumes had passed through the column. The inlet tube for the pump was then switched to the beaker containing the feed solution and the pump rate was reduced to 3.5 ml/min (0.035 bed volume). During this time the phenol was being removed from the solution and loaded onto the column. After four bed volumes of feed has been pumped through the column the inlet tube for the pump was switched to the deionized water and the pump rate was maintained at 3.5 ml/min. This continued for 4 bed volumes and the inlet tube was then switched to a stripping solution of 4% sodium hydroxide. The pump rate was maintained at 3.5 ml/min. until 4 bed volumes had passed through the column.

At the outlet of the column, samples were taken after each 0.5 bed volume during the time that phenol is loaded on the column and after each bed volume while the wash water and stripping solutions are added. It should be noted that there is a time delay between the time the inlet feed tube is changed to a new solution and this new solution leaves the bottom of the column. In each of the steps recited in these Examples the temperature was room temperature and the pressure was atmospheric pressure. The temperature of each of the solutions used in the Examples was also room temperature.

The samples are analyzed for L-2-oxothiazolidine-4-carboxylate sodium, phenol, sodium ion, and pH. The results indicated in the table set forth below were calculated.

|  | L-2-oxothiazolidine-4-carboxylate sodium | Phenol |
| --- | --- | --- |
| Feed In | 64734 mg | 25243 mg |
| Effluent Out | 64876 mg | 268 mg |
| Wash Out | 1816 mg | 13442 mg |
| Strip Out | 48 mg | 10208 mg |

Example 2

The same procedure as Example 1 was followed, except that the stripping solution was methanol. The results were as follows:

|  | L-2-oxothiazolidine-4-carboxylate sodium | Phenol |
| --- | --- | --- |
| Feed In | 67207 mg | 24829 mg |
| Effluent Out | 72291 mg | 101 mg |
| Wash Out | 2635 mg | 14133 mg |
| Strip Out | 4 mg | 11342 mg |

Example 3

The same procedure as Example 1 was followed except the adsorption resin was XAD 7. The results were as follows:

|  | L-2-oxothiazolidine-4-carboxylate sodium | Phenol |
| --- | --- | --- |
| Feed In | 61348 mg | 22566 mg |
| Effluent Out | 62178 mg | 2117 mg |
| Wash Out | 3166 mg | 20849 mg |
| Strip Out | 1436 mg | 5773 mg |

Example 4

The same procedure as Example 3 was followed except the stripping solution was methanol. The results were as follows:

|  | L-2-oxothiazolidine-4-carboxylate sodium | Phenol |
| --- | --- | --- |
| Feed In | 61348 mg | 22566 mg |
| Effluent Out | 61256 mg | 963 mg |
| Wash Out | 2460 mg | 16692 mg |
| Strip Out | 30 mg | 4477 mg |

Example 5

All of the parameters in this example were the same as Example 1 except as otherwise described herein. The feed solution in this experiment contained 1.091 kg deionized water, 0.157 kg phenol, 0.154 kg sodium chloride; 0.263 kg 1-2-oxothiazolidine-4 carboxylate sodium. A column packed with Rohm and Haas XAD-4 adsorption resin was first equilibrated with deionized water using the pumping rate of 4.2 ml/min. The feed of the simulated reaction mixture then was started and continued until four bed volumes of reaction mixture was applied to the column. Six bed volumes of wash water were then added at the same rate. After the wash was complete, the remaining phenol was stripped from the column with four bed volumes of a methanol solution at the same rate. The overall measurements gave the following mass balances:

|  | L-2-oxothiazolidine-4-carboxylate sodium | Phenol |
| --- | --- | --- |
| Feed In | 54785 mg | 24301 mq |
| Effluent Out | 56396 mg | 383 mg |
| Wash Out | 378 mg | 18680 mg |
| Strip Out | 121 mg | 4875 mg |

Example 6

This experiment was performed in a similar manner as Example 5 except that the rate of feed of the reaction mixture, the wash water, and the methanol solution was 3.5 ml/min. Also, instead of four bed volumes of reaction mixture only two bed volumes were added and instead of six bed volumes of wash water, four bed volumes were used. The results were as follows:

|  | L-2-oxothiazolidine-4-carboxylate sodium | Phenol |
| --- | --- | --- |
| Feed In | 29809 mg | 11552 mg |
| Effluent Out | 27857 mg | 0 mg |
| Wash Out | 467 mg | 7078 mg |
| Strip Out | 118 mg | 5473 mg |

Example 7

This experiment was performed in a similar manner to Example 5 except with Dow XUS 40285 adsorption resin at a flow rate of 3.5 ml/min. Four bed volumes of reaction solution, wash water, and methanol solution were used. The results were as follows:

|  | L-2-oxothiazolidine-<br>4-carboxylate sodium | Phenol |
| --- | --- | --- |
| Feed In | 59788 mg | 26543 mg |
| Effluent Out | 56407 mg | 1850 mg |
| Wash Out | 1206 mg | 9576 mg |
| Strip Out | 239 mg | 12668 mg |

In the above examples, the amounts listed under "effluent" include the outflow of the adsorption resin bed while the feed solution is added plus that which flows out of the bed during the addition of the first bed volume of wash water. The experiments were performed by including the entire bed volume eluting from the wash step to the product stream. The separation efficiencies should improve if the samples are taken every 0.5 bed volume instead after one bed volume.

The overall mass balances, i.e., input mass equals output mass, are within a difference of about only 10%, which is excellent for these experiments. In some examples more L-2-oxothiazolidine-4-carboxylate is eluting than the amount originally entering the column and in other examples more phenol is eluting than the amount originally entering the column. These discrepancies are due to standard errors in the measurements.

As is readily apparent from the experimental data, there is an excellent separation of phenol from L-2-oxothiazolidine-4-carboxylate. This is surprising since it would have been expected that a substantial amount of the L-2-oxothiazolidine-4-carboxylate would adsorb to the adsorption resin along with phenol.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

The disclosure and teachings of the art discussed in this specification are hereby incorporated by reference in their entireties.

What is claimed is:

1. A method of separating phenol from a mixture comprising L-2-oxothiazolidine-4-carboxylate and phenol which comprises contacting the mixture with a phenol adsorbing adsorption resin, the adsorption resin comprising a polymer having a polyethylene backbone and the adsorption resin is capable of adsorbing at least about 90% of the weight of phenol in the mixture while adsorbing at most about 5% of the weight of L-2-oxothiazolidine-4-carboxylate in the mixture.

2. The method of claim 1 wherein the amount of phenol adsorbed is at least about 95% to about 98% and the amount of L-2-oxothiazolidine-4-carboxylate which is adsorbed is at most about 3%.

3. The method of claim 1 further comprising separating the adsorption resin from the solution remaining after the contact.

4. The method of claim 3 further comprising acidifying the solution remaining after separation to a pH of about 1 or 2 to form L-2-oxothiazolidine-4-carboxylic acid.

5. The method of claim 4 further comprising crystallizing the L-2-oxothiazolidine-4-carboxylic acid.

6. The method of claim 4 wherein the acidification is performed with an ion-exchange adsorption resin.

7. The method of claim 1 wherein the contact is performed by passing the mixture through a column packed with the adsorption resin.

8. The method of claim 1 or 7 wherein the adsorption resin comprises a polystyrene polymer cross-linked with divinyl benzene.

9. The method of claim 1 or 7 wherein the adsorption resin comprises a polyvinylpyridine polymer cross-linked with divinyl benzene.

10. The method of claim 1 or 7 wherein the adsorption resin comprises a polyacrylic polymer.

11. The method of claim 3 further comprising washing the adsorption resin with a solvent.

12. The method of claim 11 wherein the solvent is water and/or methanol and/or an aqueous hydroxide solution.

13. The method of claim 12 wherein the aqueous hydroxide solution is sodium hydroxide.

* * * * *